United States Patent
Wu et al.

(10) Patent No.: US 12,003,892 B2
(45) Date of Patent: Jun. 4, 2024

(54) MEDICAL IMAGE ASSISTANCE SYSTEM AND MEDICAL IMAGE ASSISTANCE METHOD

(71) Applicant: Coretronic Corporation, Hsin-Chu (TW)

(72) Inventors: Chia-Chien Wu, Hsin-Chu (TW); Chen Hsiang Shih, Hsin-Chu (TW); Yi-Fa Wang, Hsin-Chu (TW); I-Han Chen, Hsin-Chu (TW)

(73) Assignee: Coretronic Corporation, Hsin-Chu (TW)

( * ) Notice: Subject to any disclaimer, the term of this patent is extended or adjusted under 35 U.S.C. 154(b) by 0 days.

(21) Appl. No.: 17/585,419

(22) Filed: Jan. 26, 2022

(65) Prior Publication Data

US 2022/0256119 A1 Aug. 11, 2022

(30) Foreign Application Priority Data

Feb. 5, 2021 (CN) .......................... 202110162894.4

(51) Int. Cl.
*H04N 7/00* (2011.01)
*A61B 90/00* (2016.01)
(Continued)

(52) U.S. Cl.
CPC .......... *H04N 7/181* (2013.01); *A61B 90/361* (2016.02); *G02B 27/0172* (2013.01);
(Continued)

(58) Field of Classification Search
CPC ........ H04N 7/181; H04N 5/272; H04N 7/183; H04N 23/57; H04N 23/80; H04N 23/90;
(Continued)

(56) References Cited

U.S. PATENT DOCUMENTS 4,907,296 A * 3/1990 Blecha .................. A42B 3/042
2/6.2
5,856,811 A * 1/1999 Shih .................... G02B 27/0176
345/8
(Continued)

FOREIGN PATENT DOCUMENTS

CN 107241579 10/2017
CN 110111875 8/2019
(Continued)

OTHER PUBLICATIONS

Ctimes, "Provide real-time information to assist AR glasses to actively deploy smart medical market", with English translation thereof, Dec. 3, 2020, pp. 1-4. Available at: https://www.ctimes.com.tw/DispNewstw.asp?O=HK4C38OONTMSAA00NA.
(Continued)

*Primary Examiner* — Frank F Huang
(74) *Attorney, Agent, or Firm* — JCIPRNET (57) ABSTRACT

A medical image assistance system and a medical image assistance method are provided. During a medical process, an image capturing apparatus located at a local location captures a first image and transmits the first image to a control device located at the local location, and the control device transmits the first image captured by the image capturing apparatus to an electronic apparatus located at a remote location. The electronic apparatus performs a marking operation on the first image to generate a second image, and transmits the second image to the control device. The control device transmits the second image to a head-mounted display apparatus located at the local location so that the head-mounted display apparatus simultaneously displays the second image and a real-time local image. The first image and the second image are at least partially the same in content.

20 Claims, 5 Drawing Sheets

(51) Int. Cl.
  *G02B 27/01*   (2006.01)
  *G16H 30/40*   (2018.01)
  *H04N 5/272*   (2006.01)
  *H04N 7/18*   (2006.01)
  *H04N 23/57*   (2023.01)
  *H04N 23/80*   (2023.01)
  *H04N 23/90*   (2023.01)
  *A61B 90/50*   (2016.01)

(52) U.S. Cl.
  CPC ............ *G16H 30/40* (2018.01); *H04N 5/272* (2013.01); *H04N 7/183* (2013.01); *H04N 23/57* (2023.01); *H04N 23/80* (2023.01); *H04N 23/90* (2023.01); *A61B 2090/365* (2016.02); *A61B 2090/373* (2016.02); *A61B 2090/502* (2016.02); *G02B 2027/0138* (2013.01); *G02B 2027/0141* (2013.01); *G02B 2027/0178* (2013.01)

(58) Field of Classification Search
  CPC .................. H04N 5/265; A61B 90/361; A61B 2090/365; A61B 2090/373; A61B 2090/502; A61B 2090/372; G02B 27/0172; G02B 2027/0138; G02B 2027/0141; G02B 2027/0178; G16H 30/40; G16H 20/40; G16H 40/67; G16H 30/20
  See application file for complete search history.

(56) References Cited

U.S. PATENT DOCUMENTS

| | | | | |
|---|---|---|---|---|
| 2014/0146153 A1* | 5/2014 | Birnkrant | ................. | H04N 7/18 348/77 |
| 2015/0009550 A1* | 1/2015 | Misago | ................ | H04N 9/3155 359/205.1 |
| 2016/0225192 A1* | 8/2016 | Jones | ..................... | G06F 3/012 |
| 2017/0007351 A1* | 1/2017 | Yu | ..................... | G02B 27/0172 |
| 2017/0099479 A1* | 4/2017 | Browd | ................... | G06F 3/011 |
| 2017/0181802 A1* | 6/2017 | Sachs | ................... | H04N 13/239 |
| 2017/0322410 A1* | 11/2017 | Watson | ................ | G06T 19/006 |
| 2018/0012413 A1* | 1/2018 | Jones | ................... | G06T 19/006 |
| 2019/0075254 A1 | 3/2019 | Jhawar et al. | | |
| 2019/0254754 A1* | 8/2019 | Johnson | ................ | G16H 20/40 |
| 2020/0117025 A1* | 4/2020 | Sauer | ...................... | G02C 9/00 |
| 2020/0330179 A1* | 10/2020 | Ton | ....................... | G02C 7/088 |
| 2021/0067764 A1* | 3/2021 | Shau | .................. | H04N 13/239 |

FOREIGN PATENT DOCUMENTS

| | | | |
|---|---|---|---|
| CN | 110795007 | | 2/2020 |
| JP | 2009092808 A | * | 4/2009 |
| TW | 201608489 | | 3/2016 |
| TW | 201612692 | | 4/2016 |
| TW | M523426 | | 6/2016 |
| TW | 201912125 | | 4/2019 |
| TW | 202000143 | | 1/2020 |
| TW | 202011888 | | 4/2020 |
| TW | 202017368 | | 5/2020 |
| TW | 202103646 | | 2/2021 |

OTHER PUBLICATIONS qingting.com, "Purdue University: AR headsets can not only assist in combat, but also help the wounded on the battlefield", with English translation thereof, Aug. 5, 2020, pp. 1-12. Available at: https://read01.com/zhtw/J83z3gL.html#.YodlYahByUk.

"Office Action of Taiwan Counterpart Application", dated May 25, 2022, p. 1-p. 7.

* cited by examiner

MEDICAL IMAGE ASSISTANCE SYSTEM AND MEDICAL IMAGE ASSISTANCE METHOD

CROSS-REFERENCE TO RELATED APPLICATION

This application claims the priority benefit of Chinese application no. 202110162894.4, filed on Feb. 5, 2021. The entirety of the above-mentioned patent application is hereby incorporated by reference herein and made a part of this specification.

BACKGROUND

Technical Field

The disclosure relates to an image processing system and method, and particularly relates to a medical image assistance system and a medical image assistance method.

Description of Related Art

Minimally invasive surgery performed with endoscopes has become prevalent among current surgical operations because of small wounds, low pain, and quick recovery among others. However, although the success rate of current operations has increased with the development of medical equipment, surgeons may inevitably encounter cases where it is necessary to discuss with other surgeons during operations. For example, during an operation, the surgeon may face a relatively challenging issue on the affected part and needs to consult an external party about the treatment. Alternatively, in an emergency, a surgeon on duty may have no choice but perform surgery on a patient and needs to discuss with the attending surgeon while performing the surgery.

Currently, it is only possible to manually take pictures and then seek external support. In addition, even after receiving instructions from an external surgeon, the surgeon has to compare the affected part with the location as instructed by the external surgeon. As such, it not only takes time to check the location of the affected part, but it also requires an experienced assistant to take the pictures. At the same time, the valuable rescue time lost may also increase a risk of infection at the affected part, or even result in failure in surgery. Accordingly, how to seek external support in time and obtain a prompt response during a medical process is currently one of the issues requiring attention.

The information disclosed in this Background section is only for enhancement of understanding of the background of the described technology and therefore it may contain information that does not form the prior art that is already known to a person of ordinary skill in the art. Further, the information disclosed in the Background section does not mean that one or more problems to be resolved by one or more embodiments of the invention was acknowledged by a person of ordinary skill in the art.

SUMMARY

The disclosure provides a medical image assistance system and a medical image assistance method, in which a surgeon can quickly and accurately treat an affected part.

The medical image assistance system of the disclosure includes an electronic apparatus located at a remote location, and an image capturing apparatus, a head-mounted display apparatus, and a control device located at a local location. The control device is coupled to the image capturing apparatus, the head-mounted display apparatus, and the electronic apparatus. During a medical process, the image capturing apparatus captures a first image and transmits the first image to the control device, and the control device transmits the first image captured by the image capturing apparatus to the electronic apparatus. The electronic apparatus performs a marking operation on the first image to generate a second image, and transmits the second image to the control device. The control device transmits the second image to the head-mounted display apparatus, such that the head-mounted display apparatus simultaneously displays the second image and a real-time local image. The first image and the second image are at least partially the same in content.

The medical image assistance method of the disclosure includes the following. During a medical process, a first image is captured by an image capturing apparatus located at a local location. By a control device located at the local location, the first image is received and transmitted to an electronic apparatus located at a remote location. By the electronic apparatus, a marking operation is performed on the first image to generate a second image, and the second image is transmitted to the control device. The second image is transmitted to a head-mounted display apparatus located at the local location by the control device. The second image and a real-time local image are simultaneously displayed by the head-mounted display apparatus. The first image and the second image are at least partially the same in content.

Based on the foregoing, the surgeon can see the actual image (the real-time local image) and the marked image (the second image) at the same time through the head-mounted display apparatus. Therefore, the surgical site of the patient can be treated quickly and accurately, the operation time can be shortened, and the accuracy and success rate of the operation can be increased.

Other objectives, features and advantages of the present invention will be further understood from the further technological features disclosed by the embodiments of the present invention wherein there are shown and described preferred embodiments of this invention, simply by way of illustration of modes best suited to carry out the invention.

To make the aforementioned more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

It is to be understood that other embodiment may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings.

In the following detailed description of a preferred embodiment with reference to the accompanying drawings, the above and other technical contents, features, and effects of the invention are clearly presented. The directional terms, such as "top", "bottom", "left", "right", "front", or "back", are used in the following embodiments with reference to the directions of the drawings for describing instead of limiting the invention.

Figure 1:
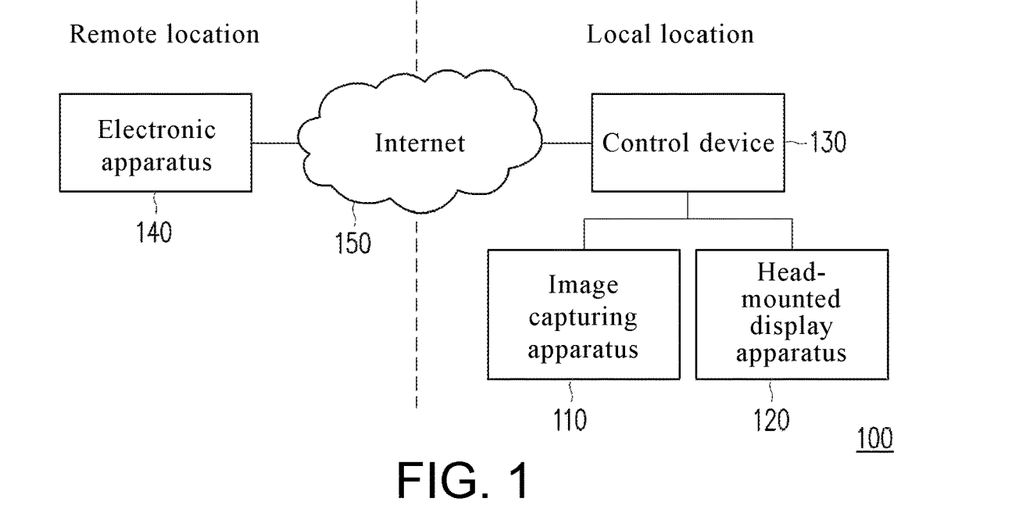
FIG. 1 is a block diagram of a medical image assistance system according to an embodiment of the disclosure.

FIG. 1 is a block diagram of a medical image assistance system according to an embodiment of the disclosure. With reference to FIG. 1, a medical image assistance system 100 includes an image capturing apparatus 110, a head-mounted display apparatus 120, and a control device 130 located at a local location. The medical image assistance system 100 also includes an electronic apparatus 140 located at a remote location. The control device 130 is coupled to the image capturing apparatus 110 and the head-mounted display apparatus 120 in a wired or wireless manner, and the control device 130 is communicated with the electronic apparatus 140 at the remote location through the Internet 150.

The image capturing apparatus 110 is, for example, a video camera or a camera adopting a charge coupled device (CCD) lens or a complementary metal oxide semiconductor transistors (CMOS) lens. The head-mounted display apparatus 120 is, for example, in the form of an eye mask or a helmet. The control device 130 is, for example, a mobile device or an image transmission processing device.

The control device 130 receives an image from or sends an image to the electronic apparatus 140 at the remote location through a communication technology protocol. The communication technology protocol is, for example, a local area network (LAN), the fourth generation of mobile communication technology standard (4G), the fifth generation of mobile communication technology standard (5G), or wireless fidelity (Wi-Fi).

For example, the image capturing apparatus 110, the head-mounted display apparatus 120, and the control device 130 are disposed in an operating room (the local location). A first image captured by the image capturing apparatus 110 is transmitted through the Internet 150 to the electronic apparatus 140 located at the remote location (e.g., the location of the user of the electronic apparatus 140) by utilizing the control device 130. A user at the remote location may perform marking on the received first image through the electronic apparatus 140, such that a second image is formed after the first image is marked, and then return the marked second image to the control device 130. The marked second image is displayed in the head-mounted display apparatus 120 through the control device 130, such that a surgeon in the operating room may see a real-time local image and the marked second image at the same time.

In an embodiment, the image capturing apparatus 110 is disposed in the head-mounted display apparatus 120. In another embodiment, the image capturing apparatus 110 is disposed in a surgical tool, and the surgical tool is connected to a medical instrument through a communication line. An image (the first image) captured by the image capturing apparatus 110 is processed by the medical instrument and then transmitted to the control device 130. In other embodiments, it is also possible to dispose the image capturing apparatus 110 in the head-mounted display apparatus 120, and dispose another image capturing apparatus in the surgical tool.

Hereinafter, steps of a medical image assistance method accompanied with the medical image assistance system 100 will be further described.

Figure 2:
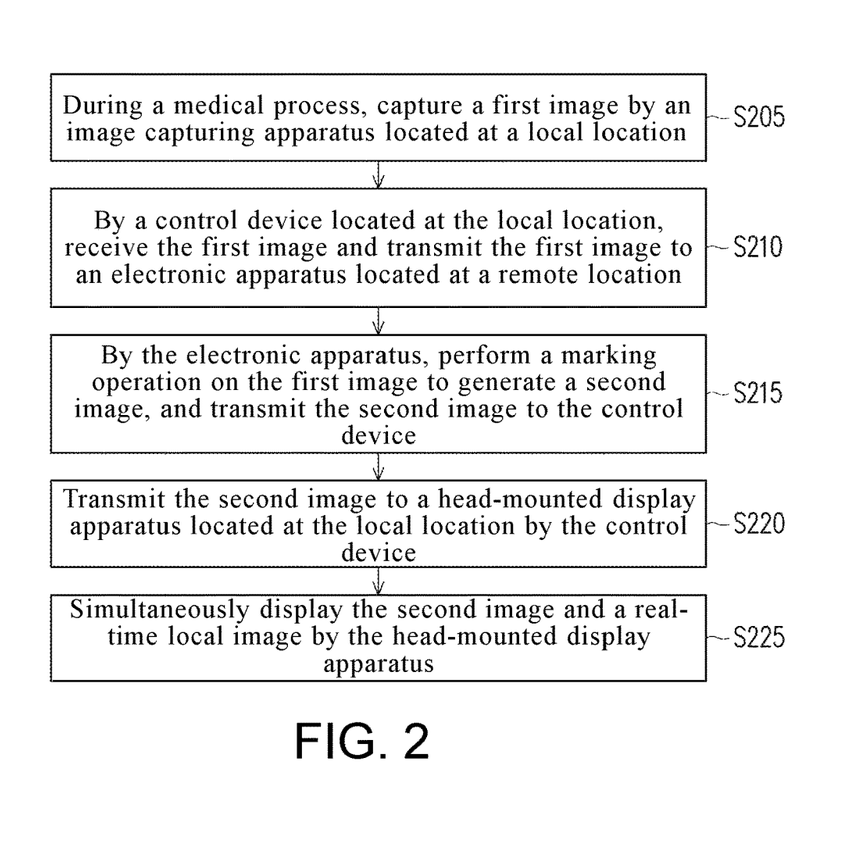
FIG. 2 is a flowchart of a medical image assistance method according to an embodiment of the disclosure.

FIG. 2 is a flowchart of a medical image assistance method according to an embodiment of the disclosure. With reference to FIG. 1 and FIG. 2 at the same time, in step S205, during a medical process, a first image is captured by the image capturing apparatus 110 located at a local location (e.g., an operating room). Herein, the first image includes a surgical site of a patient. The first image is a static image or a dynamic image.

Next, in step S210, by the control device 130 located at the local location, the first image captured by the image capturing apparatus 110 is received and transmitted to the electronic apparatus 140 located at a remote location. Herein, the control device 130 is, for example, a mobile phone, which has a first application program therein. Therefore, a user (a surgeon or an assistant in the operating room) may watch the captured images, obtain a screenshot image by the first application program, and transmit the screenshot image having the first image to the electronic apparatus 140 located at the remote location through a communication technology protocol, for example, LAN, Wifi, 4G, 5G, etc.

In other embodiments, the screenshot image may not necessarily be generated by the control device 130. It is also possible to identify a specific gesture or voice of the user through a functional module (the application program) in the head-mounted display apparatus 120 to recognize an intention of the user to generate a screenshot image, and transmit the screenshot image to the control device 130.

In step S215, by the electronic apparatus 140, a marking operation is performed on the first image to generate a second image, and the second image is transmitted to the control device 130. The second image is a static image or a dynamic image. For example, the electronic apparatus 140 is equipped with a display device and includes a second application program. An editing interface of the second application program is provided in the display device of the electronic apparatus 140, and the received first image is displayed in the editing interface. The user at the remote location performs the marking operation (hand-drawing operation, selecting operation, note creation, etc.) on the first image by utilizing the editing interface of the second application program to thereby generate the second image and transmit the second image back to the control device 130.

In step S220, the second image from the electronic apparatus 140 is transmitted to the head-mounted display apparatus 120 at the local location by the control device 130. In addition, in step S225, the second image and a real-time local image are simultaneously displayed by the head-mounted display apparatus 120. For example, the control device 130 controls the marked second image to display on the head-mounted display apparatus 120 which is worn by the surgeon, so the surgeon can see the actual image (the real-time local image) of the operation and the marked second image through the head-mounted display apparatus 120 at the same time. Herein, the first image and the second image are at least partially the same in content. For example, the second image is generated by marking the first image. Alternatively, the second image is generated by enlarging and marking the first image.

In addition, if the first image is a dynamic image (e.g., an image stream), the control device 130 sends the dynamic image to a cloud or to a local area network. The electronic apparatus 140 (e.g., a smart phone) located at the remote location downloads the dynamic image from the cloud or the local area network, such that a user (e.g., an attending surgeon) at the remote location may generate a screenshot image at a specific time point through the electronic apparatus 140 to obtain a single static image. The user at the remote location performs a marking operation on the static image through the second application program installed in the electronic apparatus 140 to obtain the second image, and transmits the second image to the cloud or the local area network. The second image (the marked image) is downloaded from the cloud or the local area network and transmitted to the head-mounted display apparatus 120 by the control device 130.

Figure 3:
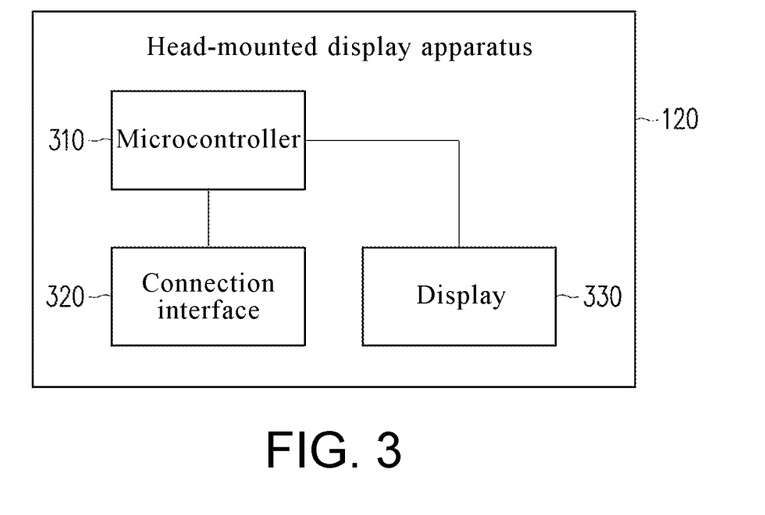
FIG. 3 is a block diagram of a head-mounted display apparatus according to an embodiment of the disclosure.

FIG. 3 is a block diagram of a head-mounted display apparatus according to an embodiment of the disclosure. With reference to FIG. 1 and FIG. 3, the head-mounted display apparatus 120 includes a microcontroller 310, a connection interface 320, and a display device 330. The microcontroller 310 is coupled to the image capturing apparatus 110, the display device 330, and the connection interface 320. The connection interface 320 is coupled to the control device 130. The connection interface 320 is, for example, Universal Serial Bus (USB) Type-C or High Definition Multimedia Interface (HDMI). The microcontroller 310 of the head-mounted display apparatus 120 receives the second image from the control device 130 through the connection interface 320, and simultaneously controls the second image and the real-time local image to be displayed into the display device 330.

Figure 4:
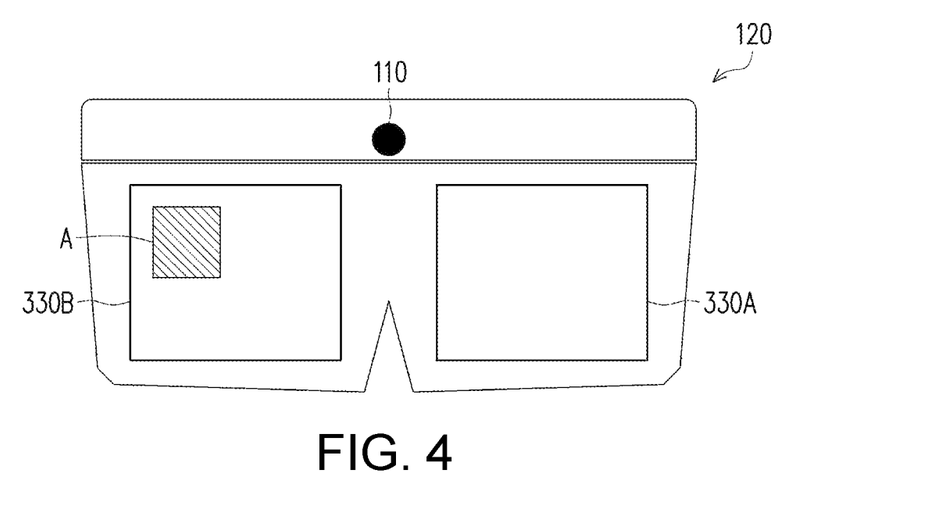
FIG. 4 is a schematic diagram of a head-mounted display apparatus according to an embodiment of the disclosure.

FIG. 4 is a schematic diagram of a head-mounted display apparatus according to an embodiment of the disclosure. With reference to FIG. 3 and FIG. 4, the image capturing apparatus 110 is disposed within the head-mounted display apparatus 120. The image capturing apparatus 110 is coupled to the microcontroller 310. The appearance of the head-mounted display apparatus 120 is typically in the form of an eye mask or a helmet. In this embodiment, the head-mounted display apparatus 120 includes augmented reality (AR) glasses, which have display devices 330A and 330B corresponding to left and right eyes respectively. The display device 330A and the display device 330B are typically two completely independent display devices, which supports the playback of stereoscopic images.

After a second image A from the control device 130 (shown in FIG. 1) is received, the second image A is overlapped and combined with the real-time local image by an optical combiner to be imaged on the display device 330B. In FIG. 4, the second image A is displayed in the display device 330B. In other embodiments, the second image A may also be displayed in the display device 330A. Since the light transmittance of the optical combiner is between 60% and 90%, the user wearing the head-mounted display apparatus 120 may see the marked image (i.e., the second image) and the real-time local image at the same time.

Figure 5:
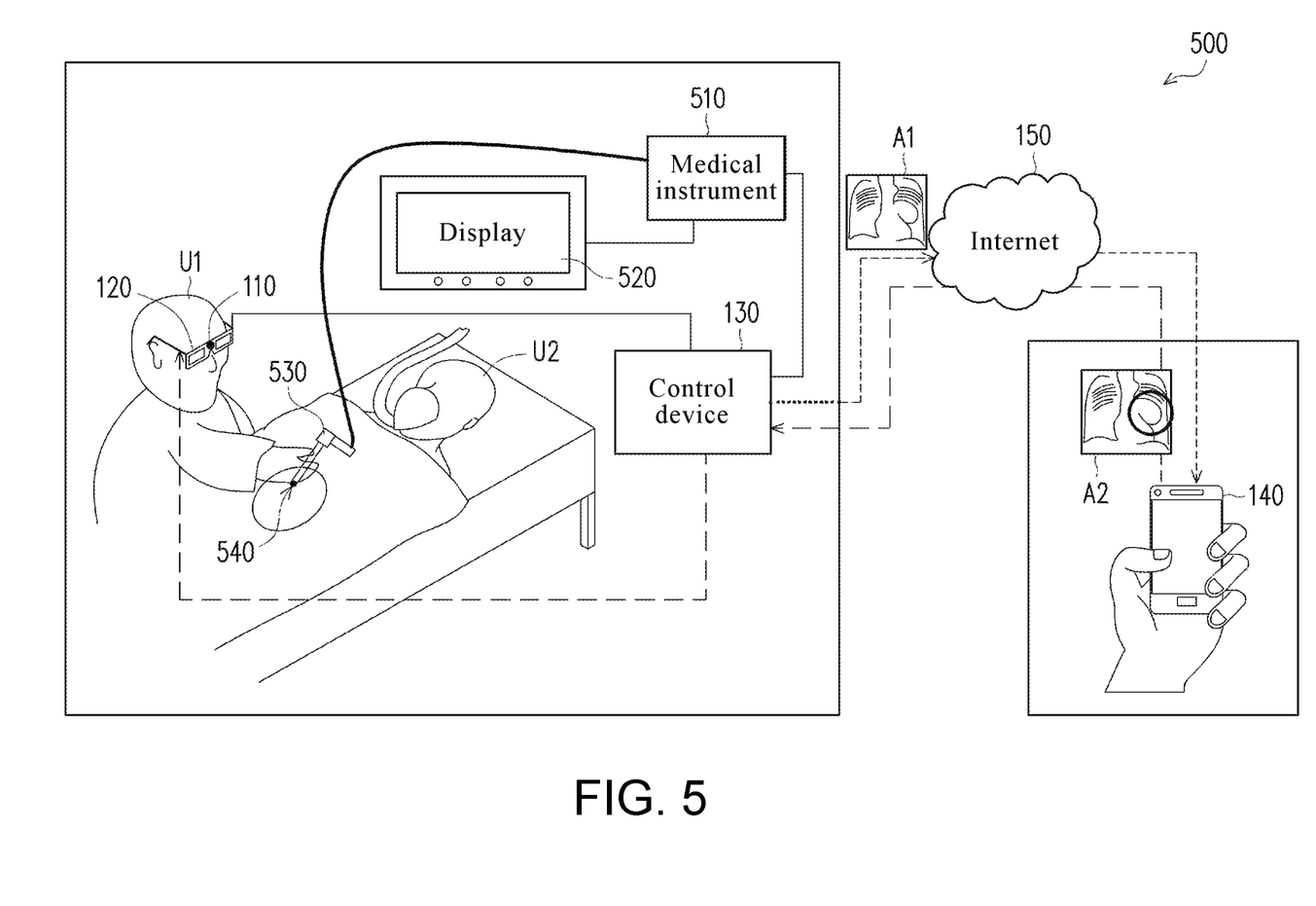
FIG. 5 is a schematic diagram of a medical image assistance system according to an embodiment of the disclosure.

FIG. 5 is a schematic diagram of a medical image assistance system according to an embodiment of the disclosure. In this embodiment, a medical image assistance system 500 further includes a medical instrument 510, a display device 520, and a surgical tool 530. In this embodiment, the head-mounted display apparatus 120, the medical instrument 510, the display device 520, and the surgical tool 530 are disposed in an operating room (a local location). The electronic apparatus 140 is located at any place (a remote location) other than the operating room, such as a remote location on another floor of the hospital.

The image capturing apparatus 110 is disposed within the head-mounted display apparatus 120. The head-mounted display apparatus 120 includes, for example, AR glasses and is worn on the face of a surgeon U1. The surgeon U1 may hold the surgical tool 530 to observe a surgical site of a patient U2. The surgical tool 530 includes another image capturing apparatus 540 disposed at one end thereof for capturing and magnifying images of the surgical site, and is connected to the medical instrument 510 at the other end through a transmission line. The surgical tool 530 may transmit a third image captured by the image capturing apparatus 540 through the transmission line to the medical instrument 510 for image processing.

The medical instrument 510 may also have a transmission line coupled to the control device 130 to transmit the third image processed by the medical instrument 510 to the control device 130.

The head-mounted display apparatus 120 and the control device 130 may also be connected through a transmission line. Accordingly, the image captured by the image capturing apparatus 110 equipped in the head-mounted display apparatus 120 is transmitted to the control device 130, or the signal transmitted from the control device 130 is displayed in the display device through the optical combiner in the head-mounted display apparatus 120 (AR glasses).

In this embodiment, the connection between the control device 130 and the medical instrument 510, or the connection between the control device 130 and the image capturing apparatus 110 may be a connection through a physical transmission line. However, in other embodiments, a wireless connection may also be adopted, which is not limited herein.

During the medical process, the third image is captured by the image capturing apparatus 540 of the surgical tool 530. The third image is transmitted to the medical instrument 510 through the transmission line of the surgical tool 530. After the third image is processed by the medical instrument 510, the processed third image is transmitted to the control device 130.

The control device 130 transmits the third image (hereinafter third image A1) captured by the image capturing apparatus 540 and processed by the medical instrument 510 through the Internet 150 to the electronic apparatus 140 at the remote location. The electronic apparatus 140 performs a marking operation on the third image A1 to generate a fourth image A2, and the electronic apparatus 140 transmits the fourth image A2 to the control device 130 through the Internet 150. The control device 130 transmits the fourth image A2 to the head-mounted display apparatus 120, such that the head-mounted display apparatus 120 simultaneously displays the fourth image A2 and the real-time local image. The third image A1 and the fourth image A2 are at least partially the same in content. For example, the fourth image is generated by marking the third image. Alternatively, the fourth image is generated by enlarging and marking the third image.

Figure 6:
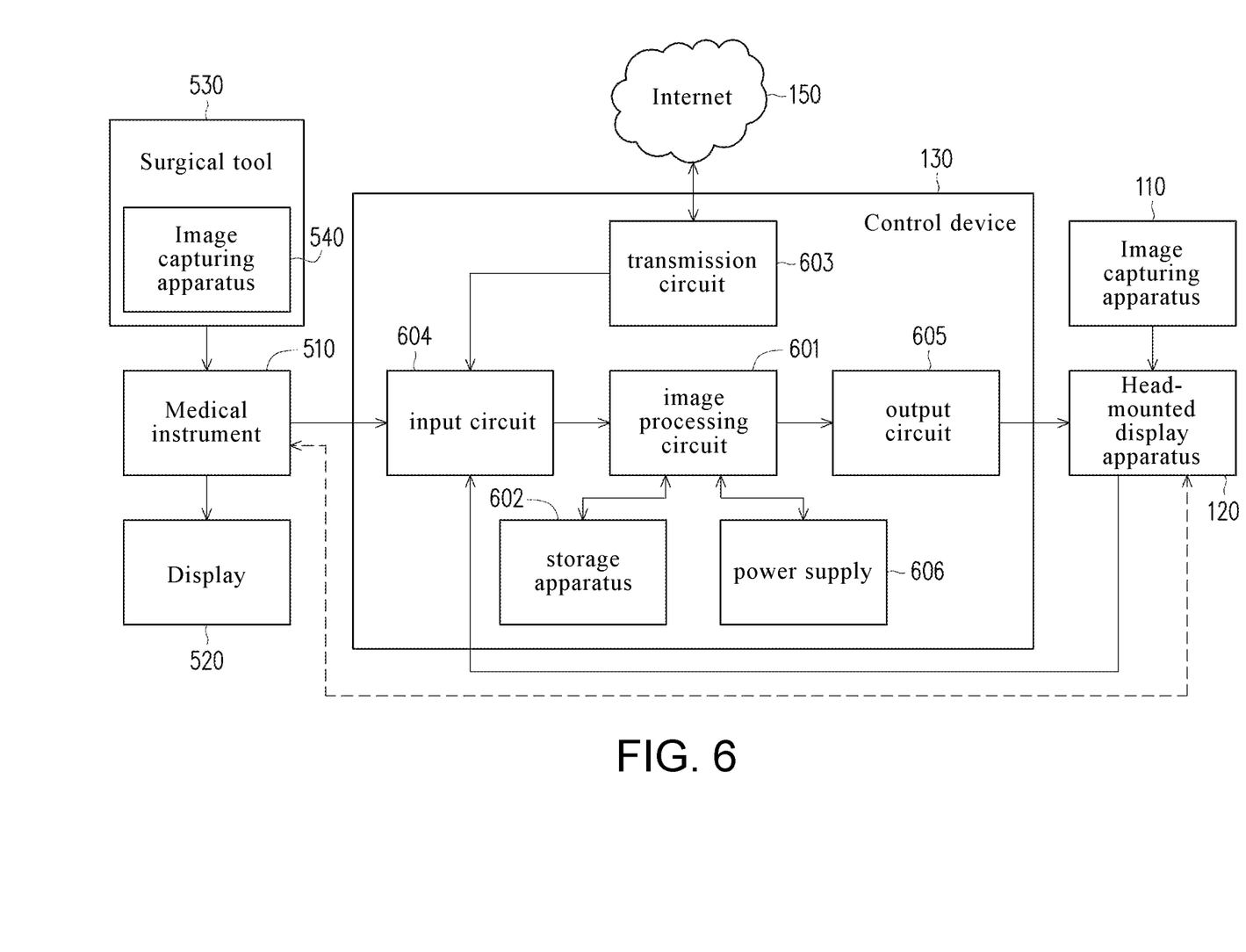
FIG. 6 is a schematic diagram of a medical image assistance system according to another embodiment of the disclosure.

FIG. 6 is a schematic diagram of a medical image assistance system according to another embodiment of the disclosure. The architecture shown in FIG. 6 is the same as the architecture shown in FIG. 5. The internal components of the control device 130 are further described in the embodiment of FIG. 6.

The control device 130 includes an image processing circuit 601, a storage apparatus 602, a transmission circuit 603, an input circuit 604, an output circuit 605, and a power supply 606. The image processing circuit 601 is coupled to the storage apparatus 602, the input circuit 604, the output circuit 605, and the power supply 606. The transmission circuit 603 is coupled to the input circuit 604.

The image processing circuit 601 is, for example, a central processing unit (CPU), a graphic processing unit (GPU), a physics processing unit (PPU), a programmable microprocessor, an embedded controller chip, a digital signal processor (DSP), an application specific integrated circuit (ASIC), or other similar devices.

The storage apparatus 602 is, for example, any form of fixed or movable random access memory, read-only memory, flash memory, secure digital card, hard disk, or other similar devices or a combination of these devices. The storage apparatus 602 is configured to store received images, and stores a first application program. The transmission circuit 603 is, for example, a network card, a WiFi chip, a mobile communication chip, and the like, configured to support communication technology protocols, such as LAN, Wifi, 4G, 5G, and the like.

The input circuit 604 is configured to receive the first image captured by the image capturing apparatus 110 in the head-mounted display apparatus 120, and may also receive the third image captured by the image capturing apparatus 540 in the surgical tool 530. The input circuit 604 may also receive, from the transmission circuit 603, an image transmitted from the remote location. The output circuit 605 is configured to transmit the image processed by the image processing circuit 601 to the head-mounted display apparatus 120. The power supply 606 is configured to supply power to maintain the operation of the control device 130.

Figure 7:
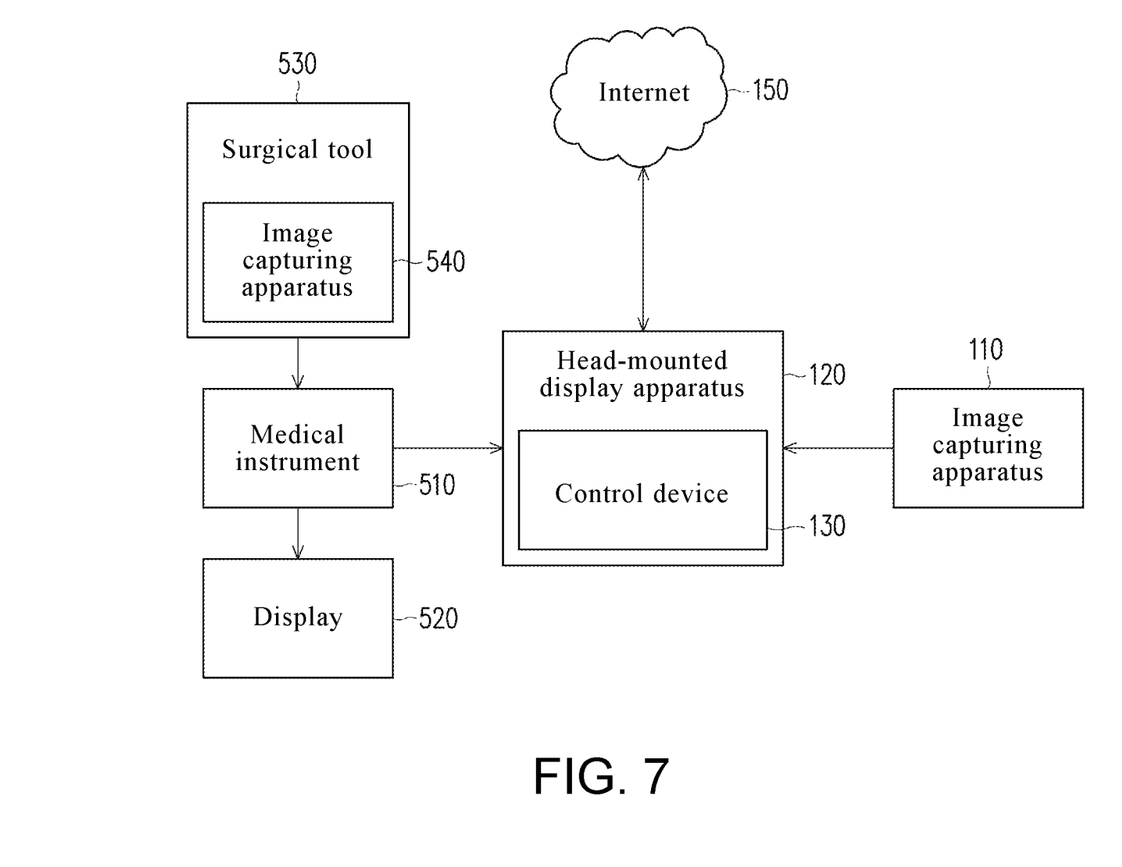
FIG. 7 is a schematic diagram of a medical image assistance system according to another embodiment of the disclosure.

FIG. 7 is a schematic diagram of a medical image assistance system according to another embodiment of the disclosure. Compared with the embodiment of FIG. 6, the embodiment of FIG. 7 is different in that, in the embodiment of FIG. 7, the control device 130 is disposed within the head-mounted display apparatus 120.

In summary of the foregoing, in the disclosure, images of the operating room (including images captured by the image capturing apparatus in the head-mounted display apparatus or images captured by the image capturing apparatus in the surgical tool) may be transmitted by the control device to the electronic apparatus at the remote location, such that the user at the remote location may perform the marking operation through the electronic apparatus, and then transmit the marked image back to the control device. The control device in turn controls the marked image to be displayed in the head-mounted display apparatus, such that the surgeon in the operating room may see the real-time local image and the marked image at the same time. Therefore, the surgical site of the patient can be treated quickly and accurately, the operation time can be shortened, and the accuracy and success rate of the operation can be increased.

The foregoing description of the preferred embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to particularly preferred exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A medical image assistance system, comprising: an electronic apparatus located at a remote location, and an image capturing apparatus, a head-mounted display apparatus, and a control device located at a local location, wherein
    the control device is coupled to the image capturing apparatus, the head-mounted display apparatus, and the electronic apparatus, wherein
    during a medical process at the local location, the image capturing apparatus located at the local location is configured to capture a first image and transmit the first image to the control device located at the local location, and the control device is configured to transmit the first image captured by the image capturing apparatus to the electronic apparatus located at the remote location;
    the electronic apparatus located at the remote location is configured to perform a marking operation on the first image to generate a marked second image, and transmit the marked second image to the control device located at the local location; and
    the control device located at the local location is configured to transmit the marked second image to the head-mounted display apparatus located at the local location, such that the head-mounted display apparatus is configured to simultaneously display the marked second image and a real-time local image for comparing a difference, wherein the first image and the marked second image are at least partially the same in content.

2. The medical image assistance system according to claim 1, wherein the image capturing apparatus is disposed in the head-mounted display apparatus, and the head-mounted display apparatus comprises:
a display device;
a connection interface, coupled to the control device; and
a microcontroller, coupled to the image capturing apparatus, the display device, and the connection interface,
wherein the microcontroller is configured to receive the marked second image from the control device through the connection interface, and control the marked second image and the real-time local image to be displayed in the display device.

3. The medical image assistance system according to claim 2, wherein the head-mounted display apparatus comprises augmented reality glasses, the display device comprises an optical combiner, and the marked second image is overlapped and combined with the real-time local image to be imaged on the optical combiner.

4. The medical image assistance system according to claim 2, wherein the control device is disposed in the head-mounted display apparatus.

5. The medical image assistance system according to claim 1, further comprising a surgical tool and a medical instrument,
wherein the image capturing apparatus is disposed in the surgical tool, the medical instrument is coupled to the control device, the surgical tool is connected to the medical instrument through a transmission line, and the first image is processed by the medical instrument and transmitted to the control device.

6. The medical image assistance system according to claim 1, wherein the control device is configured to receive or send the first image and/or the marked second image through a communication technology protocol.

7. The medical image assistance system according to claim 1, wherein the control device comprises an application program, a screenshot image is obtained by the application program from the first image captured by the image capturing apparatus, and the screenshot image having the first image is transmitted to the electronic apparatus.

8. The medical image assistance system according to claim 1, wherein the control device is a mobile device or an image transmission processing device.

9. The medical image assistance system according to claim 1, wherein the electronic apparatus located at the remote location comprises an application program, and the marking operation is performed by the application program on the first image to generate the marked second image.

10. The medical image assistance system according to claim 1, wherein the first image is a static image or a dynamic image, and the marked second image is a static image or a dynamic image.

11. The medical image assistance system according to claim 1, further comprising a surgical tool and a medical instrument,
wherein the image capturing apparatus is disposed in the head-mounted display apparatus, the surgical tool comprises another image capturing apparatus, the medical instrument is coupled to the control device, and the surgical tool is connected to the medical instrument through a transmission line, wherein during the medical process, the another image capturing apparatus is configured to capture a third image, and the third image is processed by the medical instrument and transmitted to the control device.

12. The medical image assistance system according to claim 11, wherein the control device is configured to transmit the third image captured by the another image capturing apparatus to the electronic apparatus; the electronic apparatus is configured to perform the marking operation on the third image to generate a fourth image, and transmit the fourth image to the control device; and the control device is configured to transmit the fourth image to the head-mounted display apparatus, such that the head-mounted display apparatus is configured to simultaneously display the fourth image and the real-time local image, wherein the third image and the fourth image are at least partially the same in content.

13. A medical image assistance method, comprising:
during a medical process, capturing a first image by an image capturing apparatus located at a local location;
by a control device located at the local location, receiving the first image and transmitting the first image to an electronic apparatus located at a remote location;
by the electronic apparatus located at the remote location, performing a marking operation on the first image to generate a marked second image, and transmitting the marked second image to the control device located at the local location;
transmitting the marked second image to a head-mounted display apparatus located at the local location by the control device; and
simultaneously displaying the marked second image and a real-time local image by the head-mounted display apparatus located at the local location for comparing a difference, wherein the first image and the marked second image are at least partially the same in content.

14. The medical image assistance method according to claim 13, wherein the image capturing apparatus is disposed in the head-mounted display apparatus, and the marked second image received from the control device and the real-time local image are simultaneously displayed in a display device of the head-mounted display apparatus by controlling of a microcontroller of the head-mounted display apparatus.

15. The medical image assistance method according to claim 14, wherein the head-mounted display apparatus comprises augmented reality glasses and the control device is disposed in the head-mounted display apparatus, and the step of simultaneously displaying the marked second image and the real-time local image by the head-mounted display apparatus comprises overlapping and combining the marked second image with the real-time local image to be imaged on an optical combiner of the display device.

16. The medical image assistance method according to claim 14, wherein the image capturing apparatus is disposed in a surgical tool, the surgical tool is connected to a medical instrument through a transmission line, the medical instrument is coupled to the control device, and the first image is processed by the medical instrument and transmitted to the control device.

17. The medical image assistance method according to claim 14, wherein the control device is configured to receive or send the first image and/or the marked second image through a communication technology protocol.

18. The medical image assistance method according to claim 13, wherein before the step of transmitting the first image captured by the image capturing apparatus from the control device to the electronic apparatus, the method further comprises:
    obtaining, by an application program, a screenshot image from the first image captured by the image capturing apparatus, wherein the screenshot image comprises the first image.

19. The medical image assistance method according to claim 14, wherein the step of performing the marking operation on the first image by the electronic apparatus to generate the marked second image comprises:
    performing the marking operation on the first image by an application program to generate the marked second image.

20. The medical image assistance method according to claim 14, wherein the first image is a static image or a dynamic image, and the marked second image is a static image or a dynamic image.

\* \* \* \* \*